US008704278B2

(12) United States Patent
Juang et al.

(10) Patent No.: US 8,704,278 B2
(45) Date of Patent: Apr. 22, 2014

(54) STRUCTURE FOR MOSFET SENSOR

(75) Inventors: Ying-Zong Juang, Hsinchu (TW); Hann-Huei Tsai, Hsinchu (TW); Hsin-Hao Liao, Hsinchu (TW); Chen-Fu Lin, Hsinchu (TW)

(73) Assignee: Seoul National University Industry Foundation, Seoul (KR)

( * ) Notice: Subject to any disclaimer, the term of this patent is extended or adjusted under 35 U.S.C. 154(b) by 31 days.

(21) Appl. No.: 13/419,156

(22) Filed: Mar. 13, 2012

(65) Prior Publication Data

US 2013/0153969 A1 Jun. 20, 2013

(30) Foreign Application Priority Data

Dec. 16, 2011 (TW) ............................ 100146939 A

(51) Int. Cl.
*G01N 27/403* (2006.01)
*H01L 21/00* (2006.01)

(52) U.S. Cl.
USPC ............................................ 257/253; 438/49

(58) Field of Classification Search
USPC ............... 257/252–254, 414, 419; 438/49–53
See application file for complete search history.

(56) References Cited

U.S. PATENT DOCUMENTS

| | | | | |
|---|---|---|---|---|
| 4,816,118 | A * | 3/1989 | Oyama et al. | 204/418 |
| 5,250,168 | A * | 10/1993 | Tsukada et al. | 204/416 |
| 5,309,085 | A * | 5/1994 | Sohn | 257/253 |
| 2004/0256685 | A1* | 12/2004 | Chou et al. | 257/414 |

* cited by examiner

*Primary Examiner* — Calvin Lee
(74) *Attorney, Agent, or Firm* — Morris Manning & Martin LLP; Juan Carlos A. Marquez

(57) ABSTRACT

A structure for a metal-oxide-semiconductor field-effect transistor (MOSFET) sensor is provided. The structure includes a MOSFET, a sensing membrane, and a reference electrode. The reference electrode and the sensing membrane are formed on the first surface of the MOSFET and are arranged in such a way that the reference electrode and the sensing membrane are uniformly and electrically coupled to each other. Thus, the electric field between the sensing membrane and the reference electrode is uniformly distributed therebetween to stabilize the working signal of the MOSFET sensor.

20 Claims, 10 Drawing Sheets

27
26
21
22
25
23
24
20
27
26

STRUCTURE FOR MOSFET SENSOR

BACKGROUND OF THE INVENTION

1. Technical Field

The present invention relates to the structure of a metal-oxide-semiconductor field-effect transistor (MOSFET) sensor and, more particularly, to the structure of a MOSFET sensor for use in biomedical sensing.

2. Description of Related Art

Referring to FIGS. 1A and 1B, an ion-sensitive field-effect transistor (ISFET) 100 must be provided with a reference electrode 11 in order to sense hydrogen ions or other selective ions, wherein the reference electrode 11 serves to provide the reference voltage needed by the gate of the ISFET 100. Once the surface of a sensing membrane 10 adsorbs the ions to be sensed, the original gate voltage varies such that the output current is changed. Thus, the pH value of a solution can be sensed.

As shown in FIG. 1A, when the reference electrode 11 is not integrated with the ISFET 100, the relatively long distance between the reference electrode 11 and the sensing membrane 10 gives rise to a relatively weak electric field therebetween, given the same electric potential difference. In addition, as the reference electrode 11 and the sensing membrane 10 form a parallel pair of electrodes with no gradient in the electric field therebetween, the resultant ion migration is relatively insignificant. Therefore, when the reference electrode 11 is not integrated with the ISFET 100, the position of the reference electrode 11 need not be particularly designed.

However, with the current trend toward sensor miniaturization and high integration, the conventional arrangement which requires the ISFET 100 to be connected to an external reference electrode 11 has caused inconvenience in use and prevented further downsizing. Consequently, it is difficult to integrate both the ISFET 100 and the reference electrode 11 into a micro-current system, and applications of the ISFET 100 and the reference electrode 11 are subjected to limitations.

FIG. 1B shows a prior art structure in which the reference electrode 11 and the ISFET 100 are integrated into a single chip. After integration, the reference electrode 11 and the sensing membrane 10 form a coplanar electrode structure, and yet electric field distribution between the reference electrode 11 and the sensing membrane 10 is rendered non-uniform. Moreover, due to cost and miniaturization considerations, the reference electrode 11 must be very close to the sensing membrane 10 such that the electric field therebetween is substantially increased and causes relatively significant ion migration. Such ion migration, nevertheless, tends to disturb response signals and thus impair the stability of the ISFET sensor.

BRIEF SUMMARY OF THE INVENTION

The present invention discloses a structure for a metal-oxide-semiconductor field-effect transistor (MOSFET) sensor, wherein the structure includes a MOSFET, a sensing membrane, and a reference electrode. The present invention aims to render uniform the electric field distribution between the sensing membrane and the reference electrode so that the working signal of the MOSFET sensor can be stabilized.

The present invention provides a structure for a MOSFET sensor. The structure includes: a MOSFET having a first surface; a sensing membrane formed on the first surface; and a reference electrode formed on the first surface, wherein the reference electrode and the sensing membrane are arranged in such a way that the reference electrode and the sensing membrane are uniformly and electrically coupled to each other.

Implementation of the present invention at least produces the following advantageous effects:

1. The distribution of the electric field between the sensing membrane and the reference electrode can be rendered uniform.

2. The working signal of the MOSFET sensor can be stabilized.

Hereinafter, the detailed features and advantages of the present invention are described in detail by way of the preferred embodiments of the present invention so as to enable persons skilled in the art to gain insight into the technical disclosure of the present invention, implement the present invention accordingly, and readily understand the objectives and advantages of the present invention by making reference to the disclosure of the specification, the claims, and the drawings of the present invention.

DETAILED DESCRIPTION OF THE INVENTION

Figure 1A:
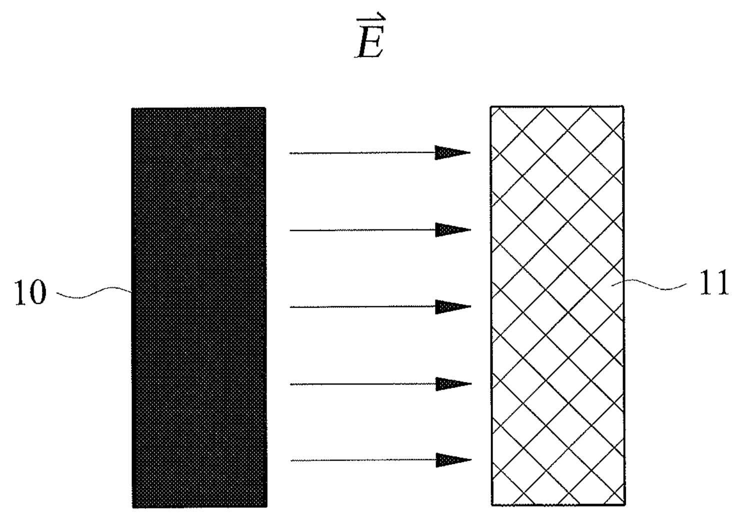
FIG. 1A schematically shows the electric field distribution between the reference electrode and the sensing membrane of a conventional ion-sensitive field-effect transistor (ISFET)
Figure 1B:
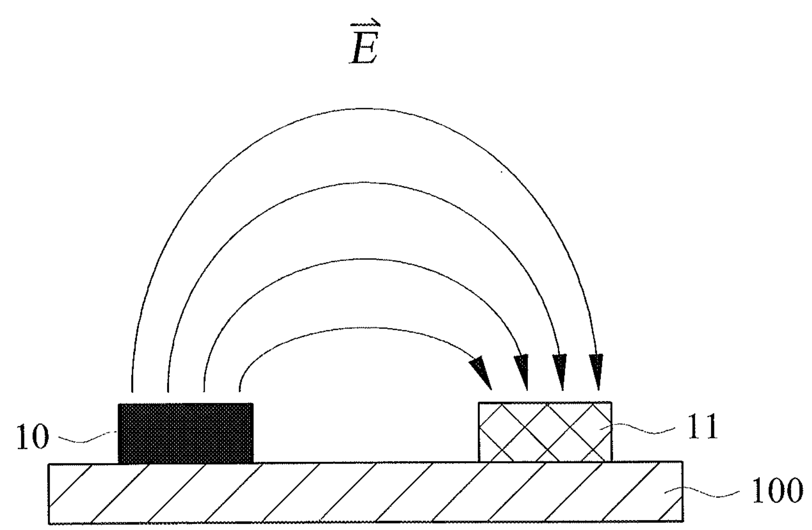
FIG. 1B schematically shows the electric field distribution between a conventional reference electrode and a conventional sensing membrane that are coplanar.
Figure 2:
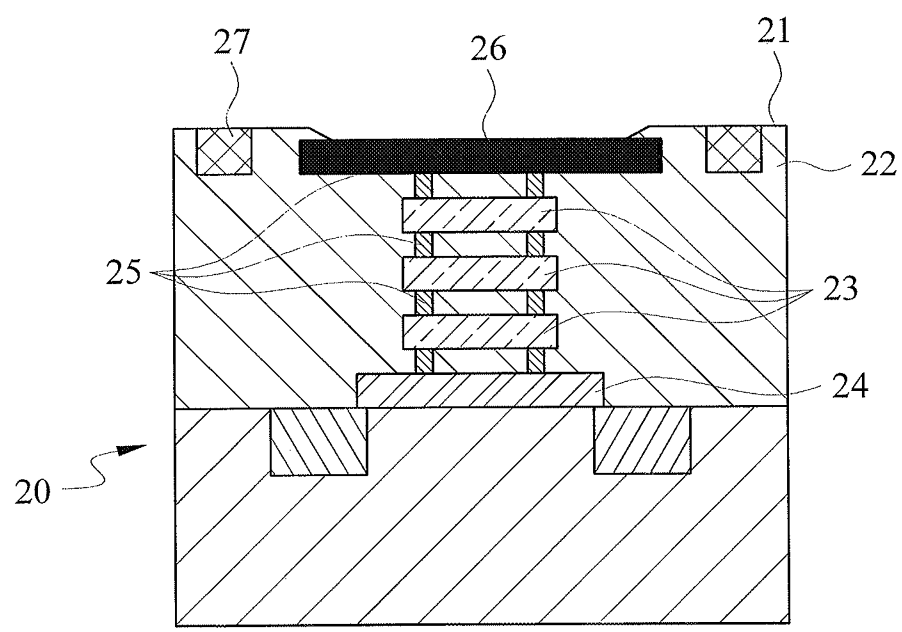
FIG. 2 schematically shows the structure of a metal-oxide-semiconductor field-effect transistor (MOSFET) sensor according to an embodiment of the present invention.

Referring to FIG. 2 for an embodiment of the present invention, a structure for a metal-oxide-semiconductor field-effect transistor (MOSFET) sensor includes a MOSFET 20, a sensing membrane 26, and a reference electrode 27.

The MOSFET 20 is configured to amplify an electric potential variation (i.e., a voltage signal) sensed by the sensing membrane 26 and then output the amplified voltage signal. The MOSFET 20 has a first surface 21, which is the upper surface of a passivation layer 22, also the uppermost layer, of the MOSFET 20 structure. The MOSFET 20 may have at least one gate metal layer 23 which is located between the sensing membrane 26 and the gate 24 of the MOSFET 20 and is parallel to the sensing membrane 26. Additionally, the at least one gate metal layer 23 has one end electrically connected to the sensing membrane 26, and the other end electrically connected to the gate 24. When there are plural gate metal layers 23, the gate metal layers 23 are parallel to one another vertically and are electrically connected by conductive posts 25 provided between each two adjacent layers.

The sensing membrane 26 is configured for sensing specific ions or biological substances. The sensing membrane 26 is formed on the first surface 21 and is formed of a specific insulating material (e.g., aluminum oxide) or an enzyme. Depending on the intended use of the MOSFET sensor, the sensing membrane 26 can be an ion-sensing membrane or a biomedical sensing membrane. When the sensing membrane 26 is an ion-sensing membrane, it can be used to sense specific ions such as hydrogen ions, potassium ions, sodium ions, calcium ions, chlorine ions, and fluorine ions. In particular, the ion-sensing membrane can be formed of a material which can form a hydrogen bond with a hydrogen ion, such as tantalum pentoxide ($Ta_2O_5$), lead titanate ($PbTiO_3$), aluminum oxide ($Al_2O_3$), silicon nitride ($Si_3N_4$), and silicon dioxide ($SiO_2$). When the sensing membrane 26 is a biomedical sensing membrane, on the other hand, it can be used to sense different biological substances such as urea and glucose. In that case, the material of which the surface of the biomedical sensing membrane is formed can be an enzyme, a DNA, a protein receptor, or like substances.

Since the sensing membrane 26 is electrically connected to the gate 24 of the MOSFET 20 by the at least one gate metal layer 23, when the sensing membrane 26 reacts with specific ions in a solution to be tested such that the electric potential on the sensing membrane 26 is changed, the variation in the electric potential will be transmitted to the gate 24 of the MOSFET 20 via the at least one gate metal layer 23, so as for the MOSFET 20 to generate the corresponding output signal.

The reference electrode 27 is also formed on the first surface 21. The reference electrode 27 and the sensing membrane 26 are arranged in such a way that they are uniformly and electrically coupled to each other. The reference electrode 27 provides the reference voltage needed by the sensing membrane 26 during operation of the MOSFET sensor. By doing so, and because the sensing membrane 26 and the gate 24 are electrically connected, the reference electrode 27 also provides the reference voltage needed by the gate 24. The material of which the reference electrode 27 is made is a substance which can provide electric potential but does not take part in reactions. Some examples of such substances are platinum, gold, and silver/silver chloride, which is formed by chlorinating the surface of silver.

Once integrated with the MOSFET sensor, the reference electrode 27 is coplanar with the sensing membrane 26. However, in order to achieve uniform distribution of the electric field between the reference electrode 27 and the sensing membrane 26, and thereby prevent the MOSFET sensor from instable operation which may otherwise occur if the ions to be sensed are interfered by a non-uniform electric field, special arrangements must be made for the sensing membrane 26 and the reference electrode 27. The various arrangements for the sensing membrane 26 and the reference electrode 27 are demonstrated hereinafter according to certain exemplary aspects of the present invention.

Figure 3:
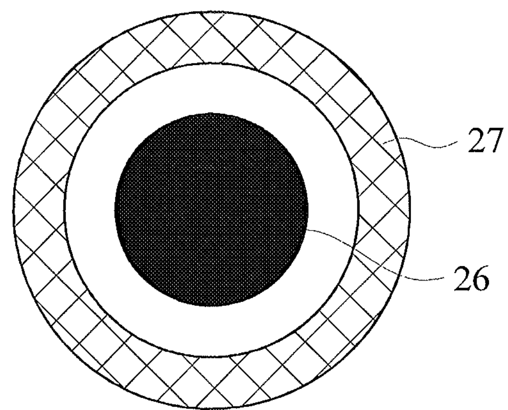
FIG. 3 shows an aspect of the present invention in which the sensing membrane and the reference electrode are shaped as a disc and a ring respectively.

Referring to FIG. 3, the sensing membrane 26 may be shaped as a disc while the reference electrode 27 is shaped as a ring and surrounds the sensing membrane 26 at a uniform spacing therefrom. More specifically, all points on the periphery of the sensing membrane 26 are radially equidistant from the inner periphery of the reference electrode 27. This allows uniform distribution of the electric field between the sensing membrane 26 and the reference electrode 27 and prevents the ions to be sensed from interference by an otherwise non-uniform electric field.

Figure 4A:
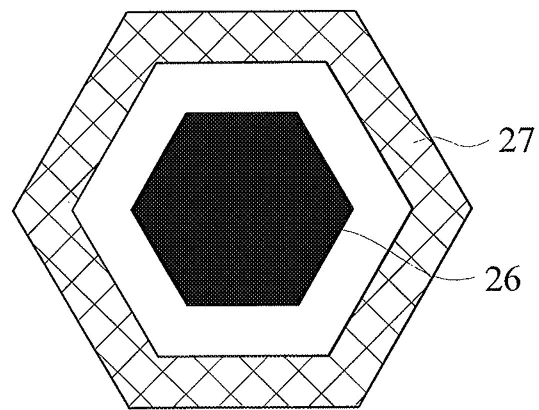
FIG. 4A shows an aspect of the present invention in which the sensing membrane and the reference electrode are shaped as a polygon and a polygonal ring respectively.

As shown in FIG. 4A, it is also feasible to shape the sensing membrane 26 as a polygon, and the reference electrode 27 as a polygonal ring that corresponds to the sensing membrane 26. In addition, the reference electrode 27 surrounds the sensing membrane 26 in such a way that the distance between each side of the polygon and the corresponding inner side of the polygonal ring is the same. This arrangement allows relatively uniform distribution of the electric field between the sensing membrane 26 and the reference electrode 27.

Figure 4B:
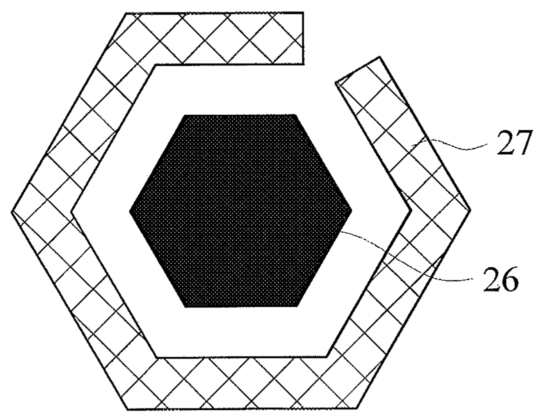
FIG. 4B shows an aspect of the present invention in which the sensing membrane is shaped as a polygon, and the reference electrode as a polygonal ring having a gap.
Figure 4C:
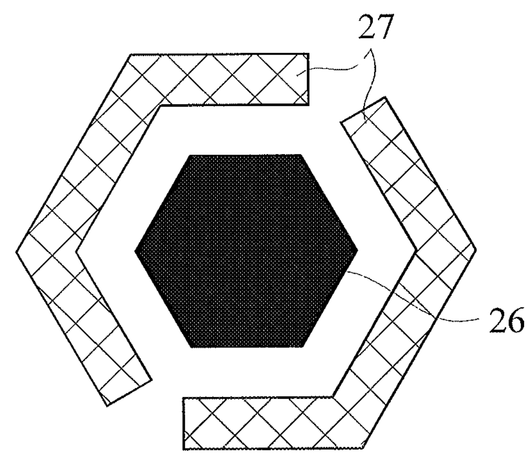
FIG. 4C shows an aspect of the present invention in which the sensing membrane is shaped as a polygon, and the reference electrode as a polygonal ring having two gaps.

Reference is now made to FIGS. 4B and 4C, in each of which drawings the sensing membrane 26 is still shaped as a polygon, and the reference electrode 27 is still shaped as a polygonal ring corresponding to and surrounding the sensing membrane 26. However, each polygonal ring is further provided with at least one gap to prevent the reference electrode 27 from forming a closed circuit. It should be noted that, while the gaps are shown as located at the corners of the polygonal rings, the gaps may be arbitrarily located on the polygonal rings as well. Thus, the reaction between the sensing membrane 26 and the ions to be sensed is kept from interference which may otherwise result if the reference electrode 27 forms a closed circuit. This allows the MOSFET sensor to be used in different application environments or situations.

Figure 5A:
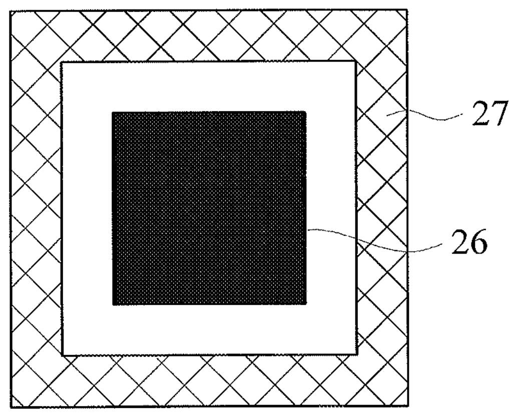
FIG. 5A shows an aspect of the present invention in which the sensing membrane and the reference electrode are shaped as a rectangle and a rectangular frame respectively.

Referring to FIG. 5A, as the foregoing polygon can be a rectangle, it is feasible to shape the sensing membrane 26 as a rectangle, and the polygonal ring-shaped reference electrode 27 as a rectangular frame that surrounds the sensing membrane 26, wherein each of the four sides of the rectangle is equidistant from the corresponding one of the four inner sides of the rectangular frame. This arrangement also allows the electric field between the sensing membrane 26 and the reference electrode 27 to be distributed in a relatively uniform manner.

As shown in FIGS. 3, 4A, and 5A, the reference electrode 27 may surround the sensing member 26 entirely such that a closed circuit is formed. However, the current in the closed circuit will generate a magnetic field at the center of the circuit (i.e., at the sensing membrane 26), and the magnetic field may, in some cases, interfere with the reaction between the sensing membrane 26 and the ions to be sensed. To solve this problem, the arrangement of the sensing membrane 26 and the reference electrode 27 can be further modified as follows.

Figure 5B:
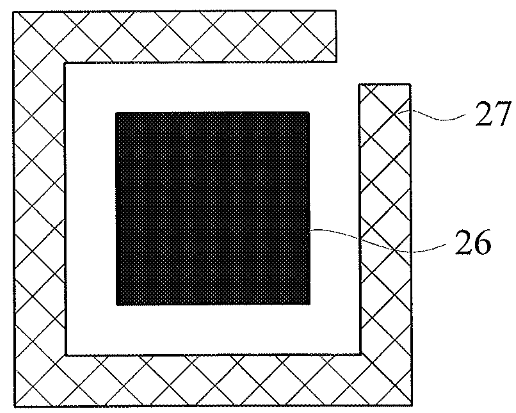
FIG. 5B shows an aspect of the present invention in which the sensing membrane is shaped as a rectangle, and the reference electrode as a rectangular frame having a gap.
Figure 5C:
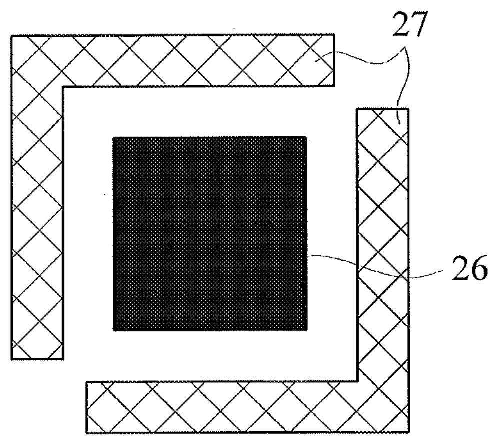
FIG. 5C shows an aspect of the present invention in which the sensing membrane is shaped as a rectangle, and the reference electrode as a rectangular frame having two gaps.

Referring to FIGS. 5B and 5C, the sensing membrane 26 is shaped as a rectangle, and the reference electrode 27, though still shaped as a rectangular frame surrounding the sensing membrane 26, further has at least one gap located at a right-angle corner of the rectangular frame, thus preventing the reference electrode 27 from forming a closed circuit. It should be noted that the at least one gap need not be located at a right-angle corner of the rectangular frame and can be provided at an arbitrary position of the rectangular frame. Consequently, the reaction between the sensing membrane 26 and the ions to be sensed is kept from interference which may otherwise result from the closed circuit formed by the reference electrode 27, and this allows the MOSFET sensor to be used in different application environments or situations.

Figure 6:
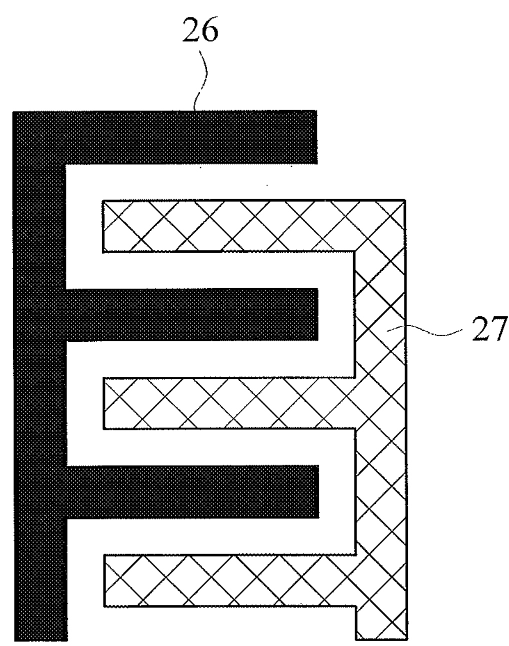
FIG. 6 shows a first aspect of the present invention in which the sensing membrane and the reference electrode are arranged in an interdigitating manner.
Figure 7:
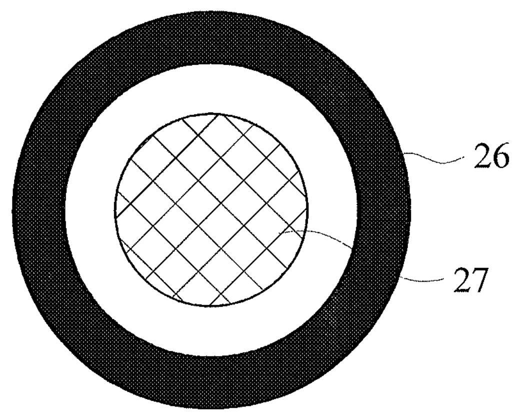
FIG. 7 shows an aspect of the present invention in which the sensing membrane and the reference electrode are shaped as a ring and a disc respectively.
Figure 8A:
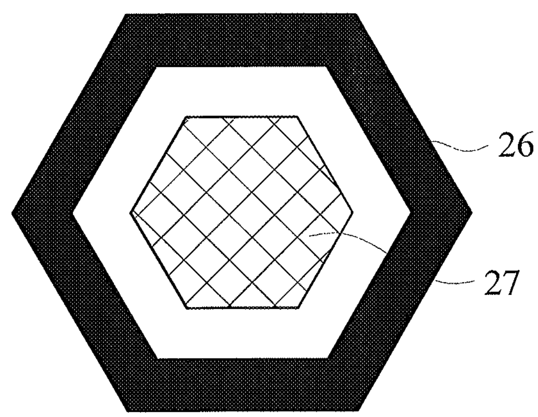
FIG. 8A shows an aspect of the present invention in which the sensing membrane and the reference electrode are shaped as a polygonal ring and a polygon respectively.
Figure 8B:
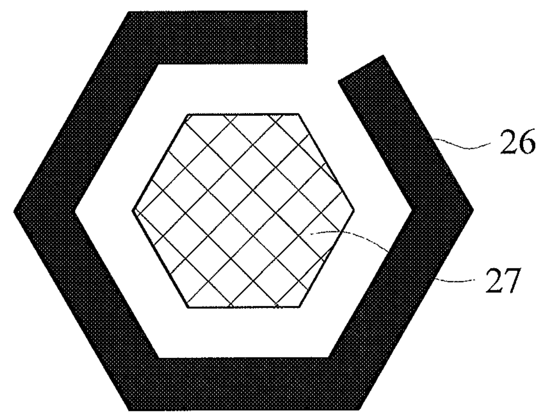
FIG. 8B shows an aspect of the present invention in which the sensing membrane is shaped as a polygonal ring having a gap, and the reference electrode as a polygon.
Figure 8C:
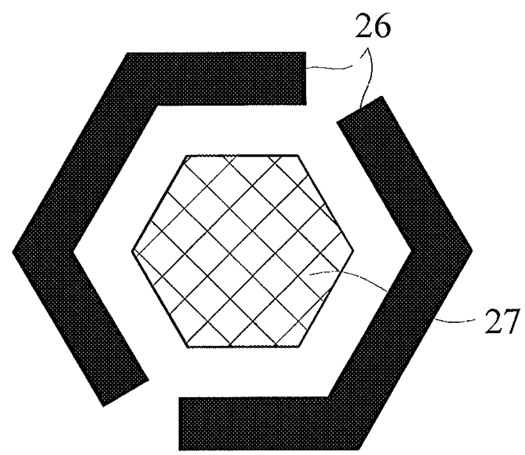
FIG. 8C shows an aspect of the present invention in which the sensing membrane is shaped as a polygonal ring having two gaps, and the reference electrode as a polygon.
Figure 9A:
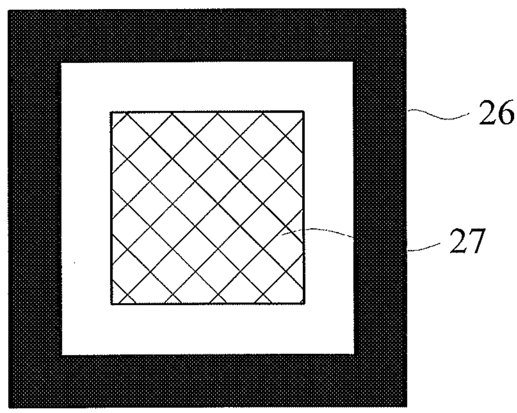
FIG. 9A shows an aspect of the present invention in which the sensing membrane and the reference electrode are shaped as a rectangular frame and a rectangle respectively.
Figure 9B:
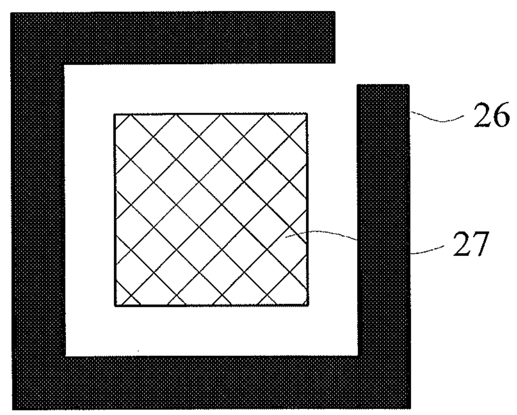
FIG. 9B shows an aspect of the present invention in which the sensing membrane is shaped as a rectangular frame having a gap, and the reference electrode as a rectangle.
Figure 9C:
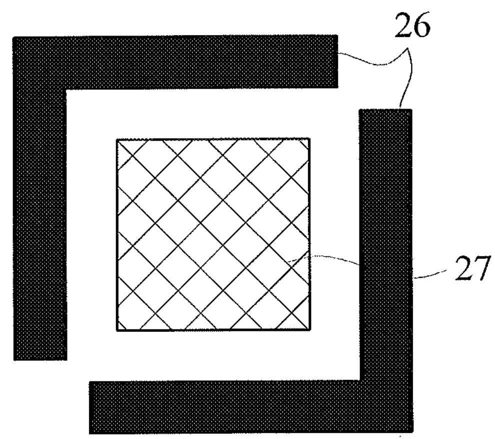
FIG. 9C shows an aspect of the present invention in which the sensing membrane is shaped as a rectangular frame having two gaps, and the reference electrode as a rectangle.

Referring to FIG. 6, the sensing membrane 26 and the reference electrode 27 may also be arranged in an interdigitating manner in which the corresponding sides of the sensing membrane 26 and of the reference electrode 27 are equally spaced to ensure that the electric field between the sensing membrane 26 and the reference electrode 27 is uniformly distributed in most areas therebetween.

While the arrangements shown in FIGS. 4B, 4C, 5B, 5C, and 6 can keep the reference electrode 27 from forming a closed circuit and prevent the reaction between the sensing membrane 26 and the ions to be sensed from interference, it is further required that, in cases where the reference electrode 27 only partially surrounds the sensing membrane 26, the portion of the sensing membrane 26 that is surrounded by the reference electrode 27 be greater than 50% of the sensing membrane 26. This is to ensure that the sensing area between the sensing membrane 26 and the reference electrode 27 is large enough for sensing a sufficient amount of ions, so as to produce significant voltage variation. Therefore, when the reference electrode 27 only surrounds a portion of the sensing membrane 26, it is important that the portion is greater than 50% of the sensing membrane 26; only then can the MOSFET sensor successfully sense such physical quantities as the concentration of ions or of a biological substance.

Figure 10:
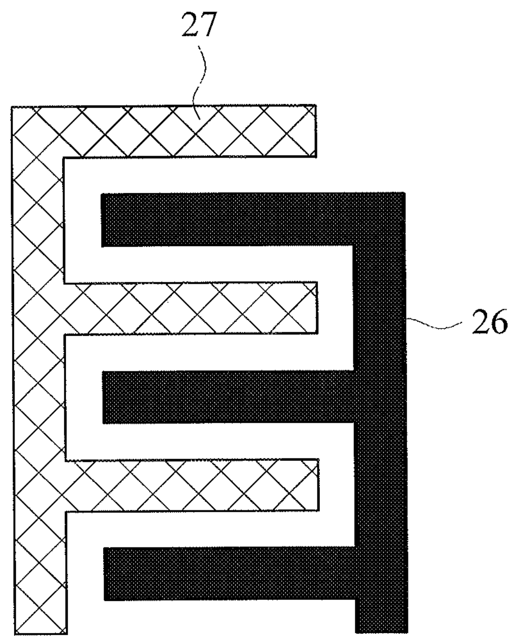
FIG. 10 shows a second aspect of the present invention in which the sensing membrane and the reference electrode are arranged in an interdigitating manner.

The arrangement of the sensing membrane 26 and the reference electrode 27 is not limited to having a certain one of them surrounding the other; that is to say, the aforesaid positions of the sensing membrane 26 and of the reference electrode 27 are interchangeable. For example, referring to FIGS. 7 through 10, the reference electrode 27 may be surrounded by the sensing membrane 26, wherein the reference electrode 27 is disc-shaped, and the sensing membrane 26 is ring-shaped; or wherein the reference electrode 27 is shaped as a polygon, and the sensing membrane 26 as a polygonal ring corresponding to the reference electrode 27. In the latter case, the reference electrode 27 may be shaped as a rectangle, and the sensing membrane 26 as a rectangular frame. Moreover, the polygonal ring may further have at least one gap which, in cases where the sensing membrane 26 is a rectangular frame, is located at a right-angle corner of the rectangular frame. In addition, referring to FIG. 10, the sensing membrane 26 and the reference electrode 27 may be arranged in an interdigitating manner different from that shown in FIG. 6.

While the arrangements shown in FIGS. 8B, 8C, 9B, 9C, and 10 can keep the sensing membrane 26 from forming a closed circuit and prevent the reaction between the reference electrode 27 and the ions to be sensed from interference, it is further required that, in cases where the sensing membrane 26 only partially surrounds the reference electrode 27, the portion of the reference electrode 27 that is surrounded by the sensing membrane 26 be greater than 50% of the reference electrode 27. This is to ensure that the sensing area between the sensing membrane 26 and the reference electrode 27 is large enough for sensing a sufficient amount of ions, so as to produce significant voltage variation. Therefore, when the sensing membrane 26 only surrounds a portion of the reference electrode 27, it is important that the portion is greater than 50% of the reference electrode 27; only then can the MOSFET sensor successfully sense such physical quantities as the concentration of ions or of a biological substance.

In any of the structures described above, the reference electrode 27 is integrated with the MOSFET 20 to complete the manufacture of the MOSFET sensor. The major advantage of integration with the MOSFET 20 is that a reading circuit can be easily integrated to further downsize the MOSFET sensor. Moreover, by forming the sensing membrane 26 and the reference electrode 27 into particular shapes and arranging them in particular ways, the electric field between the sensing membrane 26 and the reference electrode 27 will remain uniform almost everywhere therebetween. Thus, the targets (e.g., ions) to be sensed are prevented from interference otherwise attributable to a non-uniform electric field, and the integrated MOSFET sensor will stay stable during operation.

The features of the present invention are disclosed above by the preferred embodiments to allow persons skilled in the art to gain insight into the contents of the present invention and implement the present invention accordingly. The preferred embodiments of the present invention should not be interpreted as restrictive of the scope of the present invention. Hence, all equivalent modifications or amendments made to the aforesaid embodiments should fall within the scope of the appended claims.

What is claimed is:

1. A structure for a metal-oxide-semiconductor field-effect transistor (MOSFET) sensor, the structure comprising:

a MOSFET having a first surface;

a sensing membrane formed on the first surface; and a reference electrode formed on the first surface, wherein the reference electrode and the sensing membrane are formed and positionally shaped relative to each other on the first surface such that all peripheral portions of one of the reference electrode and the sensing membrane are substantially equidistant to corresponding peripheral portions of the other of the reference electrode and the sensing membrane, and the reference electrode and the sensing membrane are uniformly coupled to each other via an electric field that is formed therebetween.

2. The structure of claim 1, wherein the sensing membrane is an ion-sensing membrane.

3. The structure of claim 2, wherein the ion-sensing membrane is formed of a material capable of forming a hydrogen bond with a hydrogen ion, the material being selected from the group consisting of tantalum pentoxide ($Ta_2O_5$), lead titanate ($PbTiO_3$), aluminum oxide ($Al_2O_3$), silicon nitride ($Si_3N_4$), and silicon dioxide ($SiO_2$).

4. The structure of claim 1, wherein the sensing membrane is a biomedical sensing membrane.

5. The structure of claim 4, wherein the biomedical sensing membrane has a surface formed of an enzyme, a DNA, or a protein receptor.

6. The structure of claim 1, wherein the MOSFET has at least a gate metal layer electrically connected between the sensing membrane and a gate of the MOSFET.

7. The structure of claim 1, wherein the reference electrode is made of platinum, gold, or silver/silver chloride.

8. The structure of claim 1, wherein the sensing membrane is shaped as a disc, and the reference electrode is shaped as a ring and surrounds the sensing membrane at a uniform spacing therefrom.

9. The structure of claim 1, wherein the reference electrode is shaped as a disc, and the sensing membrane is shaped as a ring and surrounds the reference electrode at a uniform spacing therefrom.

10. The structure of claim 1, wherein the sensing membrane is shaped as a polygon, and the reference electrode is shaped as a polygonal ring corresponding to the sensing membrane and surrounds the sensing membrane.

11. The structure of claim 10, wherein the polygon is a rectangle, and the polygonal ring is a rectangular frame.

12. The structure of claim 10, wherein the polygonal ring further has at least a gap.

13. The structure of claim 12, wherein the polygon is a rectangle, the polygonal ring is a rectangular frame, and each said gap is located at a right-angle corner of the rectangular frame.

14. The structure of claim 1, wherein the reference electrode is shaped as a polygon, and the sensing membrane is shaped as a polygonal ring corresponding to the reference electrode and surrounds the reference electrode.

15. The structure of claim 14, wherein the polygon is a rectangle, and the polygonal ring is a rectangular frame.

16. The structure of claim 14, wherein the polygonal ring further has at least a gap.

17. The structure of claim 16, wherein the polygon is a rectangle, the polygonal ring is a rectangular frame, and each said gap is located at a right-angle corner of the rectangular frame.

18. The structure of claim 1, wherein the sensing membrane and the reference electrode are arranged in an interdigitating manner.

19. The structure of claim 1, wherein the reference electrode surrounds a portion of the sensing membrane, the portion being greater than 50% of the sensing membrane.

20. The structure of claim 1, wherein the sensing membrane surrounds a portion of the reference electrode, the portion being greater than 50% of the reference electrode.

* * * * *

UNITED STATES PATENT AND TRADEMARK OFFICE

CERTIFICATE OF CORRECTION

PATENT NO. : 8,704,278 B2
APPLICATION NO. : 13/419156
DATED : March 13, 2012
INVENTOR(S) : Juang et al.

It is certified that error appears in the above-identified patent and that said Letters Patent is hereby corrected as shown below:

Title Page, Column 1, under Item (73) Assignees:

Delete
"Seoul National University Industry Foundation, Seoul, Republic of Korea"

Add
--National Chip Implementation Center National Applied Research Laboratories, Hsinchu City, Taiwan--

Signed and Sealed this
Twentieth Day of May, 2014

Michelle K. Lee
*Deputy Director of the United States Patent and Trademark Office*